(12) United States Patent
Lorenz et al.

(10) Patent No.: US 8,577,441 B2
(45) Date of Patent: Nov. 5, 2013

(54) SYSTEM AND METHOD FOR IMAGE BASED PHYSIOLOGICAL MONITORING OF CARDIOVASCULAR FUNCTION

(75) Inventors: Christine H Lorenz, Frederick, MD (US); Corinna Maier, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1285 days.

(21) Appl. No.: 11/635,101

(22) Filed: Dec. 7, 2006

(65) Prior Publication Data

US 2007/0135705 A1 Jun. 14, 2007

Related U.S. Application Data

(60) Provisional application No. 60/749,558, filed on Dec. 12, 2005.

(51) Int. Cl.
*A61B 5/05* (2006.01)

(52) U.S. Cl.
USPC .......................................................... 600/410

(58) Field of Classification Search
USPC .......................................................... 600/410
See application file for complete search history.

(56) References Cited

U.S. PATENT DOCUMENTS

| | | | | |
|---|---|---|---|---|
| 5,734,739 A | * | 3/1998 | Sheehan et al. | 382/128 |
| 5,797,396 A | * | 8/1998 | Geiser et al. | 600/407 |
| 6,015,384 A | * | 1/2000 | Ramamurthy et al. | 600/440 |
| 6,064,768 A | * | 5/2000 | Hajj et al. | 382/195 |
| 6,295,464 B1 | * | 9/2001 | Metaxas | 600/407 |
| 6,317,620 B1 | * | 11/2001 | Ho et al. | 600/419 |
| 6,780,152 B2 | * | 8/2004 | Ustuner et al. | 600/443 |
| 7,158,692 B2 | * | 1/2007 | Chalana et al. | 382/294 |
| 7,561,909 B1 | * | 7/2009 | Pai et al. | 600/410 |
| 2003/0174872 A1 | | 9/2003 | Chalana | |
| 2004/0153128 A1 | * | 8/2004 | Suresh et al. | 607/14 |
| 2005/0008209 A1 | * | 1/2005 | Matsumoto | 382/128 |

OTHER PUBLICATIONS

C.H. Lorenz, et al. "*Interactive Frontend (IFE): A Platform for Graphical MR Scanner Control and Scan Automation*" Proc., Int'l Soc. Mag. Reson. Med. 13 (2005).

* cited by examiner

*Primary Examiner* — Jacqueline Cheng
(74) *Attorney, Agent, or Firm* — Donald B. Paschburg; F. Chau & Associates, LLC

(57) ABSTRACT

A method for real time monitoring of cardiac function includes defining a plurality of planes through a heart from which to acquire heart imaging data, acquiring a sequence of 2-dimensional images from said selected planes, wherein each said image comprises a plurality of intensities defined on a domain of points on a 2D grid, selecting one or more of said sequence of images to provide imaging data for monitoring heart function, wherein said remaining unselected images are adapted for diagnostic purposes, and repeating said steps of acquiring a sequence of 2-dimensional images from said selected planes and selecting one or more of said sequence of images for monitoring heart function, wherein a time sequence of images is obtained, alternating between images for monitoring heart function and images for diagnostic purposes.

28 Claims, 7 Drawing Sheets

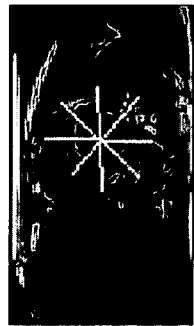
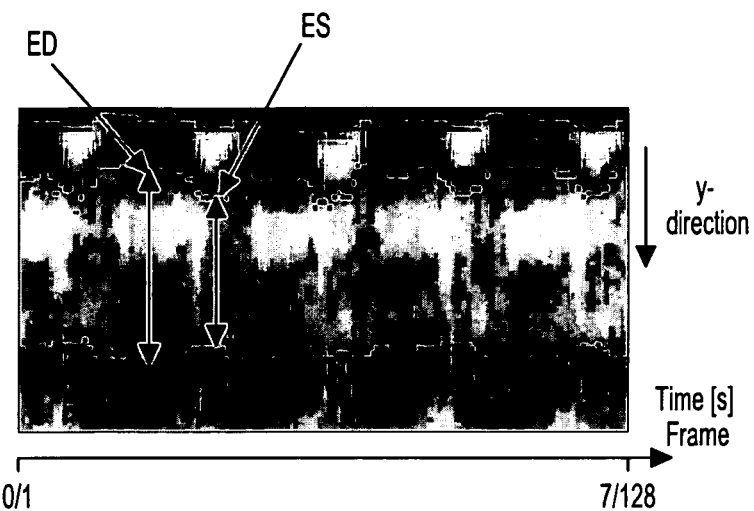
FIG. 3(A)  FIG. 3(B)
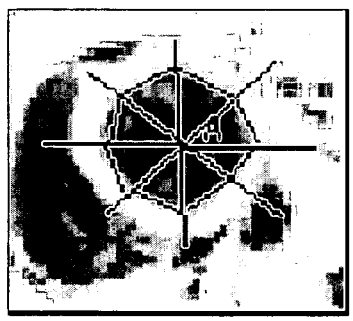
FIG. 3(C)

FIG. 6(A)   FIG. 6(B)

SYSTEM AND METHOD FOR IMAGE BASED PHYSIOLOGICAL MONITORING OF CARDIOVASCULAR FUNCTION

CROSS REFERENCE TO RELATED UNITED STATES APPLICATIONS

This application claims priority from: "Image Based Physiological Monitoring of Cardiovascular Function", U.S. Provisional Application No. 60/749,558 of Lorenz, et al., filed Dec. 12, 2005, the contents of which are incorporated herein by reference.

TECHNICAL FIELD

This invention is directed to real-time monitoring of heart function using magnetic resonance imaging (MRI), interleaved with imaging used to guide or perform stress testing or interventional cardiovascular procedures.

DISCUSSION OF THE RELATED ART

Monitoring the electrocardiogram (ECG) for ischemic changes during dobutamine stress testing or an MR-guided intervention is not possible in the MR environment due to the magnetohydrodynamic effect. This effect occurs because ions in the blood flowing through the body in the presence of a static magnetic field create its own electrical voltage. This additional voltage is added to the ECG when the patient is inside the static magnetic field, causing distortion. However, during MR guided cardiovascular interventional procedures or during stress testing, cardiac function should be monitored for possible ischemic changes or dyssynchrony. Wall motion and global cardiac function can be assessed in real time by MR and interleaved with other types of MR acquisitions during the procedure. One approach to monitoring for ischemic changes therefore would be to qualitatively assess wall motion in the images as they are acquired. However, in the time gaps where the physician cannot view the functional images (during ramp-up of dobutamine dose, or while placing a catheter for example), it would be useful to have a measure of cardiac function automatically determined and provided as continuous feedback.

The main challenge in patient monitoring for ischemia in MRI is that the static magnetic field, RF pulses, and field gradient switching all distort the ECG making it non-diagnostic for ischemia detection. Ischemia in the heart first results in a perfusion deficit, then in abnormalities in wall motion, then ECG changes, then finally in chest pain. Currently, external monitoring systems with ECG, blood pressure, pulse oximetry and sometimes invasive blood pressure are used in conjunction with MR for global patient monitoring. ECG can be used to monitor only the heart rate. During interventional procedures, changing the real time scan plane is used to check for changes in function, but this does not provide continuous monitoring. Visual review of perfusion scans during acquisition also can be used to check for changes in heart perfusion, but these cannot be repeated as often during an exam as ventricular function imaging since they require contrast agent administration.

However, converting real time MR into an m-mode (motion mode) representation analogous to echocardiography could allow (a) a simple continuous display of cardiac function and (b) simplify real time segmentation and automatic extraction of ventricular function parameters. Although the concept of interleaving types of MR imaging methods is exploited in the field of navigator gating, where a low resolution image is used to sample bulk motion and is interpreted to either gate an acquisition, or to shift a slice position, the inventors have found no publications regarding interleaving physiological monitoring scans with imaging scans.

SUMMARY OF THE INVENTION

Exemplary embodiments of the invention as described herein generally include methods and systems for real-time assessment of cardiac function by 2D MR imaging. Cardiac function can be assessed visually, or displayed as m-mode data to enable assessment of the temporal history as well. The m-mode display and resulting measurements can be interleaved with other types of acquisition and incorporated into a real time interface for scanner control. A system and method of an embodiment of the invention enable early ischemia detection based on wall motion, using real time imaging interleaved with 'standard' imaging. By interleaving MR data acquisition one can use a portion of the data for direct heart function monitoring, on a continuous basis, while the rest of the data are used for diagnostic or interventional purposes. Wall motion and ventricular function parameters are extracted from the real time imaging, and methods for change detection alert the operator that heart function has changed. In addition to monitoring for ischemia, methods according to embodiments of the invention can be used to detect changes in patterns of contraction (due to conduction abnormalities), detect changes in cardiac output (real time flow imaging), or changes in patterns of perfusion (real time myocardial perfusion imaging). Embodiments of the invention extract relevant features from the interleaved monitoring data, and identify clinically relevant changes to assist the operator in monitoring heart function. A system according to an embodiment of the invention for real-time image interleaving can provide near-continuous monitoring of heart function in the MR environment where ECG is not diagnostic. In addition, it can potentially provide more sensitive feedback on changes in heart function than global ECG monitoring could provide, independent of its use in an MRI environment. This potentially increased sensitivity stems from the fact that both wall motion changes and myocardial perfusion changes precede ECG changes during ischemia. The concept of using direct measurement of heart function in the background while some other diagnostic procedure or therapeutic imaging is being performed can also be applied to other imaging modalities, such as computed tomography (CT) or ultrasound (US).

Validation results show the feasibility of a real time method for global left ventricle function assessment that can be combined with stress testing or interventional procedures. Integration into a real time environment using 1-2 slices for function monitoring and additional temporally interleaved slices for procedure guidance is feasible.

BRIEF DESCRIPTION OF THE DRAWINGS

FIGS. 3(A)-(C) depicts an exemplary short axis slice with m-mode projections shown, and the derived contours superimposed on m-mode display, according to an embodiment of the invention.

DETAILED DESCRIPTION OF THE PREFERRED EMBODIMENTS

Figure 1:
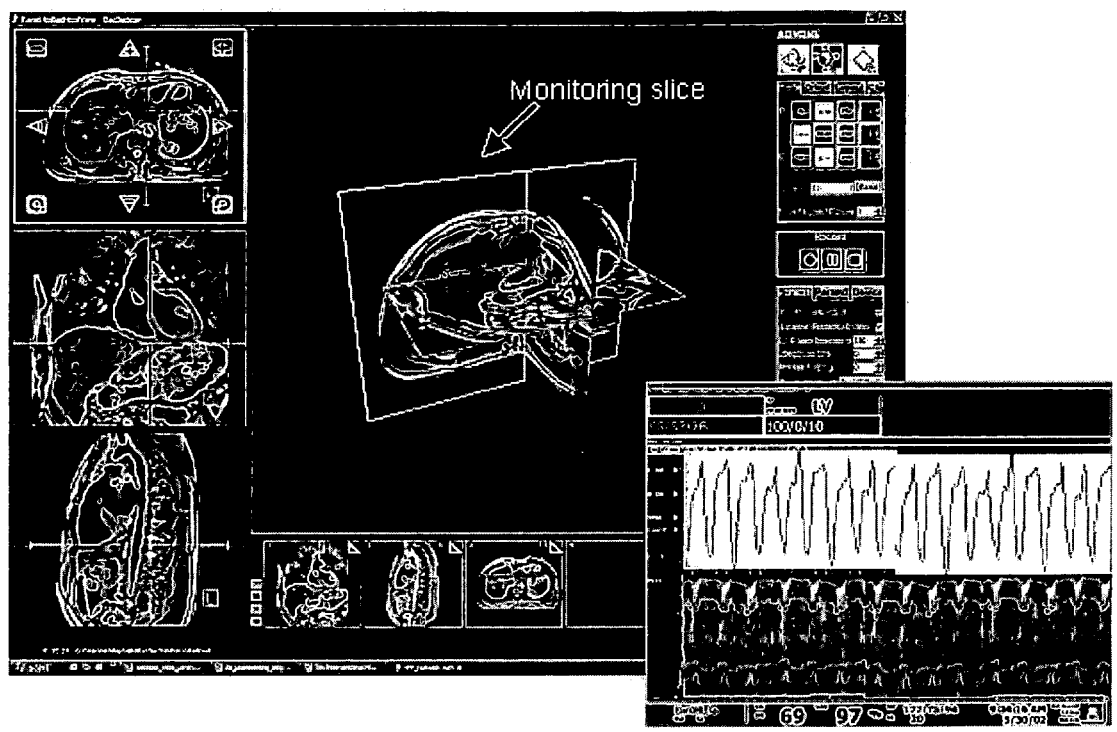
FIG. 1 illustrates one exemplary real-time heart function imaging/monitoring configuration, according to an embodiment of the invention.

Exemplary embodiments of the invention as described herein generally include systems and methods for real-time monitoring of heart function using magnetic resonance imaging (MRI), interleaved with imaging used to guide or perform stress testing or interventional cardiovascular procedures. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computed tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A system according to an embodiment of the invention includes imaging data acquired in an interleaved manner, with part of the data used to monitor heart function, and the rest used for diagnostic purposes, such as guiding a procedure, methods for extracting relevant features from the images related to heart function, such as endocardial and epicardial borders, volume flow through the aorta, change in shape of the ventricle, myocardial perfusion, etc., and methods for detecting clinically relevant changes in the aforementioned features and alerting an operator.

A scanning frontend provides a user interface (UI) that allows both control of the scan plane orientation and also selection of imaging parameters based on feature extraction from previously acquired images, or from any general parameter optimization algorithm.

A scanning frontend according to an embodiment of the invention can be developed by modification of existing, commercially available software. An exemplary, non-limiting frontend was developed using a combination of RadBuilder, available from Siemens Corporate Research, modified with additional C++ code. A family of manipulators created in RadBuilder limits motion of the slices in the 3D window to constrained motion to prevent the user from losing orientation while moving the slices. Slice manipulation is allowed in one of several modes: free rotation and translation, in plane rotation, rotation about slice center, and translation along the slice normal.

The frontend application can run on an independent workstation connected via ethernet to a scanner host computer, or can run directly on the scanner host computer. The frontend application can communicate with the current open running protocol via socket communications to a custom application running on the host. Through this application, slice manipulation performed graphically in 3D on the frontend application is transformed into scanner coordinates and sent to the running protocol to update the slice position. After image acquisition the image reconstruction program sends the image data both to the standard database and also via socket communication back to the frontend application.

The main viewing window of the UI can be used for visualizing renderings made from previously acquired images in addition to display of newly acquired slices in real time. An exemplary UI has windows on the left used for two dimensional slice positioning and viewing of both previous images and realtime updates, and small windows on the bottom containing a history of acquisitions already made. These images can be moved to the lefthand windows or the main viewing/manipulating window as needed. The frontend includes at least two modes of operation: (1) visualization, where movement of the imaging planes in the main window does not result in any scanner update, and (2) active slice manipulation where movement of the scan planes.

According to an embodiment of the invention, one or more 2D images can be positioned in a plane to monitor heart functions, such as heart wall motion and flow in the heart. The 2D images need not be in the same place. FIG. 1 illustrates one exemplary, non-limiting imaging/monitoring configuration, with one monitoring slice and two imaging slices that are mutually orthogonal, as indicated in the central 3D view. The 3 panels on the left side are the three 2D views, with the monitoring view at the top. The panel in the lower right corner is a graph of monitoring data derived from the monitoring slice, such as wall motion, heart dimensions, flow, perfusion, etc., as a function of time (horizontal axis).

MR images can be acquired in real-time with a temporal resolution currently of about 30-50 ms. Complete images can be acquired and interleaved in time, as opposed to the interleaving of partial data being used to form an image over multiple interleaves. There is thus is no reduction of resolution of the final images.

In one exemplary timeline, a temporal acquisition sequence might look like M, I, M, I, M, I, . . . , where M represents an image acquired for monitoring, and I represents an image acquired for standard imaging. This acquisition sequence in which every other image is used for monitoring is non-limiting, and in general, every $n^{th}$ image can be used for monitoring. In a real time case, the only difference between monitoring images and imaging images would be their location in the heart—the monitoring images can be acquired at a user pre-selected location of interest or automatically as determined by other algorithms to focus on areas of high risk, and the imaging slices can be focused on other parts of the heart as selected by a user, or automatically.

The user can position the images freely and identify the images as those to be used for monitoring. Additional image planes can be positioned by the user to be used for diagnostic purposes, or for guiding an interventional procedure. The monitoring images would then be analyzed on a continuous basis or at intervals determined by the user during scanning for the extraction of heart function parameters.

Figure 2:
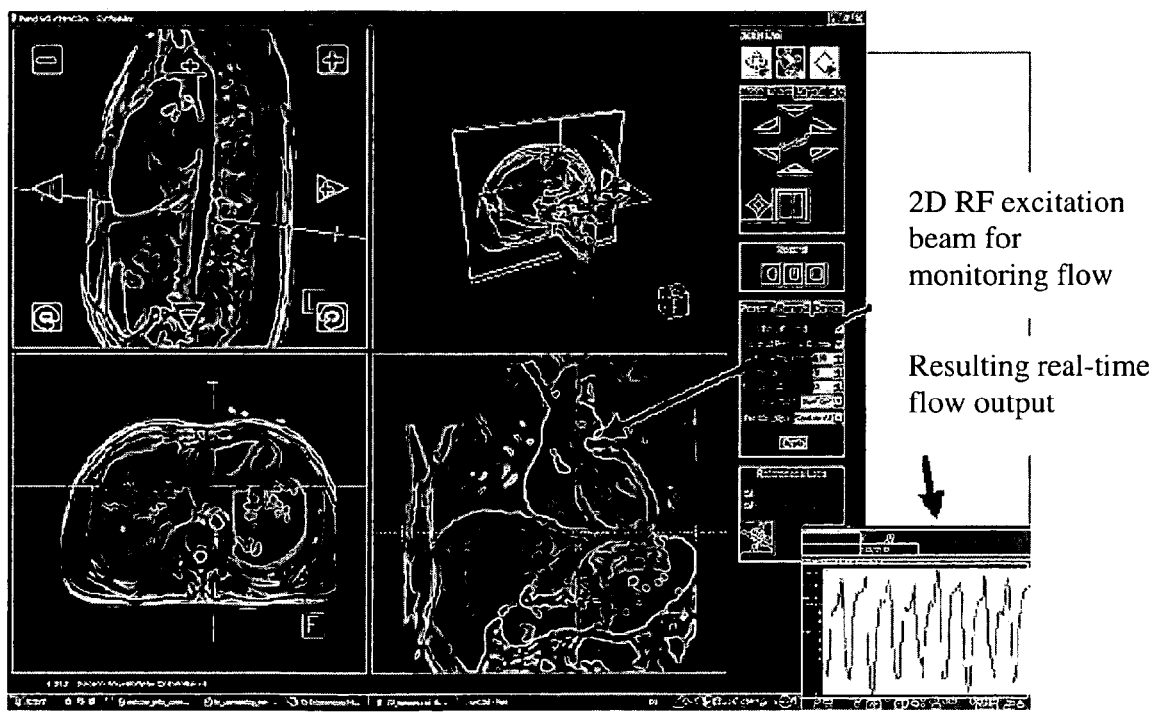
FIG. 2 illustrates an exemplary image-based monitoring configuration for 2D radio-frequency (RF) excitation for real-time flow measurement, according to an embodiment of the invention.

FIG. 2 illustrates an exemplary image-based monitoring configuration for 2D radio-frequency (RF) excitation for real-time flow measurement interleaved with multi-slice imaging. The upper right panel is a 3D view showing how the imaging and monitoring slices are positioned with respect to the heart, while the lower right panel is a view of the monitoring slice (the x-y plane through the heart), with the position of the 2D RF excitation beam as indicated. The graph at the lower right corner depicts the real-time flow output as determined by the excitation beam. The excitation beam could also be replaced with a 2D slice with flow encoding.

To optimize a tradeoff between speed and accuracy of the calculated heart function parameters, the user of a system would be able to define desired measurement accuracy. Depending on the accuracy, the system will automatically adjust the spatial and temporal sampling. The spatial sampling includes the number of parallel slices, the image resolution for one slice and the number of projections in case of a 1D method. The temporal resolution is defined as the number of acquired time frames per slice/projection in one heart cycle.

According to an embodiment of the invention, real time MR is converted to an m-mode (motion mode) representation analogous to echocardiography that allows a simple continuous display of cardiac function and simplifies real time segmentation and automatic extraction of ventricular function parameters. An m-mode display according to an embodiment of the invention can be incorporated into a real time interface for scanner control.

Figure 5:
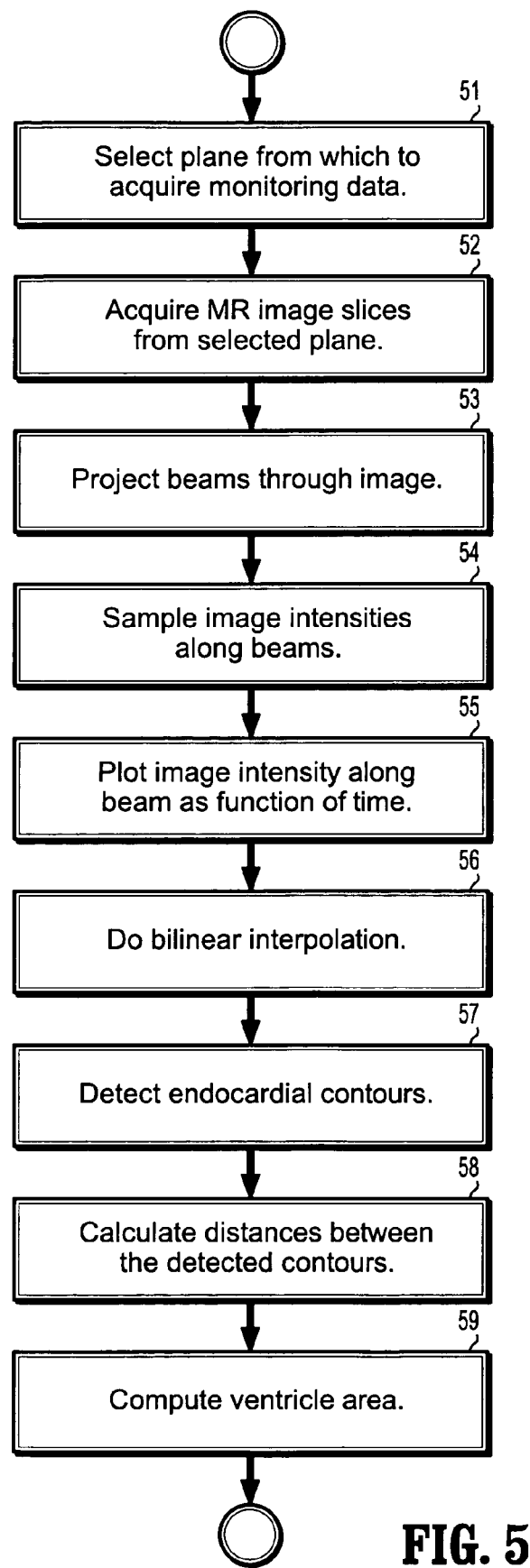
FIG. 5 is a flowchart of a method for real-time extraction of heart function parameters using m-mode MR, according to an embodiment of the invention.

FIG. 5 is a flowchart of a method for real-time extraction of heart function parameters using m-mode MR, according to an embodiment of the invention. Referring now to the figure, at step 51, for the m-mode MR creation, a user manually selects a plane through the heart from which to acquire monitoring data, and locates the center of the left ventricle on a single short axis slice. As MR image slices are acquired at step 52, four equiangular projections are propagated through the ventricle at step 53 as m-mode projection beams, intersecting the ventricle in 45 degree segments. Each image slice is periodically sampled at step 54 for its intensity along the beams, which form substantially collinear subsets of points. According to an embodiment of the invention, these projections are one pixel wide. As a temporal sequence of image slices are acquired, the image intensity along each beam ($M_{i,t}$) is plotted at step 55 as a function of time. In order to increase the number of grid points, as well as for smoothing, a bilinear interpolation is performed at step 56. In each beam $M_{i,t}$ the endocardial contours are detected at step 57.

According to an embodiment of the invention, the contours are detected using a modified horizontal 1D-Canny Filter. Smoothing is performed using a 1D Gaussian in the y-direction with $\sigma=1$, and the gradient calculation is based on the second derivative of the above Gaussian in the y-direction. The Canny thresholds are estimated depending on the histogram of $M_{i,t}$; and it is assumed in this embodiment of the invention that 75% of the pixels do not belong to the heart wall.

According to another embodiment of the invention, the epicardial contours can be detected using an active contour model, also known as a "snake" algorithm. The active contour model minimizes an image energy function. This energy function $$E=\lambda E_{int}+\gamma E_{img}$$

of the snake model is expressed in terms of external, constraint forces $E_{img}$, depending on the image, and of internal constraint forces $E_{int}$, depending on the shape of the contour. $E_{int}$ is the weighted addition of two terms based on the first and second snake derivatives representing elasticity and bending forces acting on the contour. $E_{img}$ comprises a linear combination of the image gradient in vertical direction and low pass filtered zero-crossings. In the applied open snake model the coordinate values in the horizontal axis are those integer numbers representing the time point of the m-mode projection, and these values are fixed. Only the position values on the vertical axis of a snake point can move.

For snake initialization the endocardial contour is translated in the direction of the expected epicardial contour. Minimizing the energy function causes the active contour to converge.

The distances between the detected endocardial contours are calculated at step 58. The maximum distances (as a function of time) in each projection are taken as the LV end-diastolic (ED) diameter, while the minimum distances are taken as the end-systolic (ES) diameters.

According to an embodiment of the invention, wall contour data is used to estimate the ejection fraction in the slice (EF). In this embodiment, referring again to FIG. 5, the area of the ventricle is computed at ED and ES for each heartbeat at step 59 using the area enclosed by the 8 vertices of the endocardial contour. The ejection fraction EF is then calculated as $$EF(\%) = 100 \times \frac{EDV - ESV}{EDV},$$

where EDV is the end-diastolic ventricle area and ESV is the end-systolic ventricle area.

Tests of embodiments of the invention were performed using data acquired from three healthy subjects. Short axis real time images midway between the mitral valve plane and the papillary muscle level during free breathing were acquired using a TrueFISP (SSFP) sequence, TE/TR/Flip angle 0.87/1.74/60, FOV=160×380 mm², matrix 88×128, GRAPPA acceleration×2, slice thickness 8 mm, temporal resolution 54 ms, 128 frames.

As an initial validation, the m-mode-derived contour data were superimposed on the real time images with the vertex points and viewed as a cine-loop for visual confirmation. Contours were also displayed on the m-mode display for visual inspection, to compare results against an EF based on manually drawn contours to estimate statistically significant differences. FIG. 3(A) illustrates an exemplary short axis (SA) slice with the 8 m-mode projections shown, and FIG. 3(B) shows the derived contours superimposed on an m-mode display, with an ED diameter and an ES diameter shown as indicated. FIG. 3(C) depicts the SA slice with superimposed triangles for computing the ventricle area. The visual qualitative inspection of the m-mode-derived contours on the m-mode display, depicted in FIG. 3(B), show good correspondence. The average area EF for the subjects was in the range 55-70% as expected for normal EF. Beat to beat variation in EF was in the range of 2-9%. Thus, no statistically significant difference was found between an EF estimation method according to an embodiment of the invention and an EF calculation based on manually drawn contours in single slices, although only single slice estimates of EF tested.

This method of an embodiment of the invention for calculating area ejection fraction can be expanded for an automatic measurement of local wall thickness and percent wall thickening. Automated methods of assessing wall thickness in real time can provide a platform for computer assisted change detection during interventional procedures or stress testing. The wall thickness for each time point is calculated as the distance between the endocardial position value and the epicardial position value. The epicardial contour can be calculated using the same algorithms used for the endocardial contour.

Figure 4:
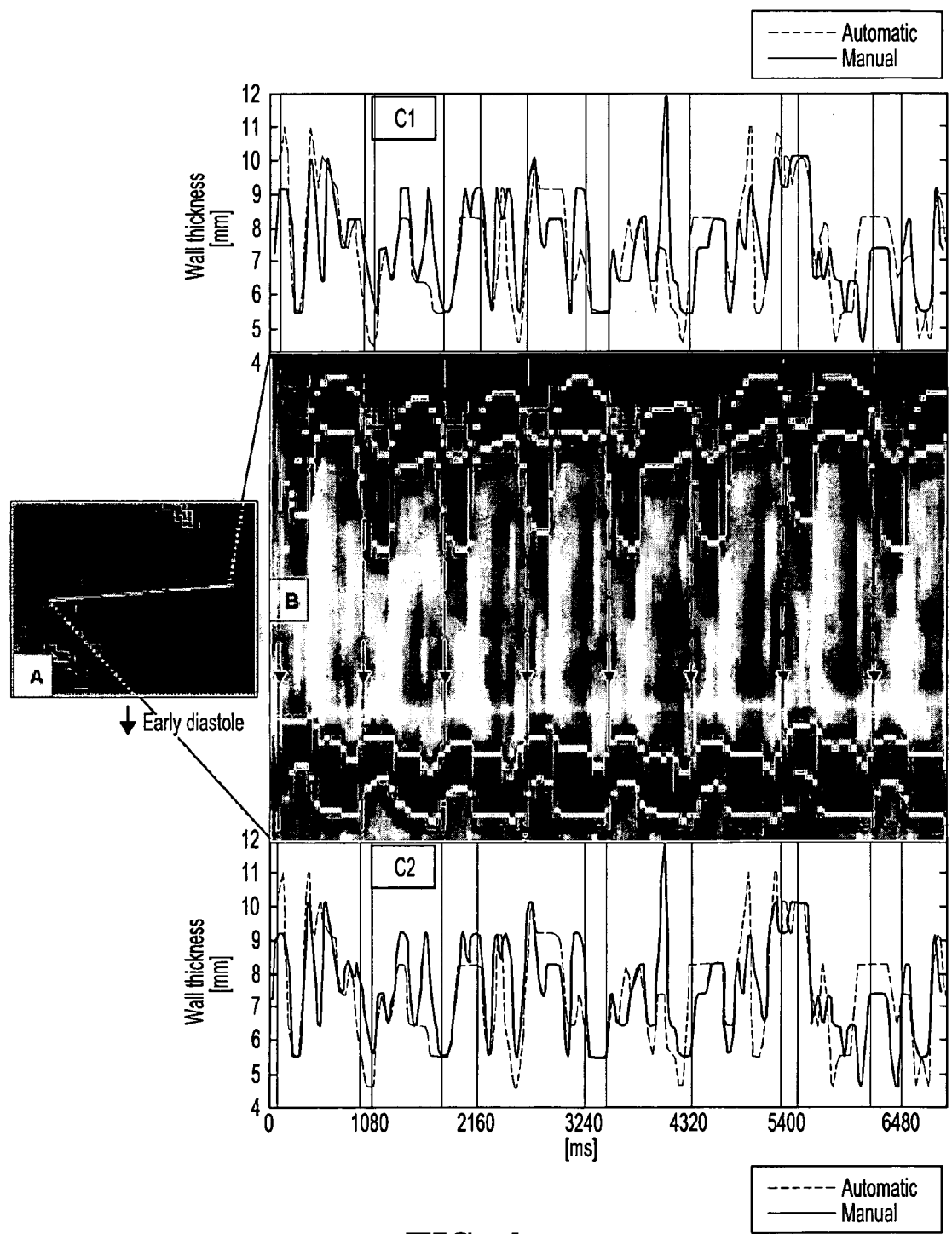
FIGS. 4(A)-(C2) depict contours displayed on an MRI m-mode for visual assessment of accuracy, according to an embodiment of the invention.

FIGS. 4(A)-(C2) illustrate contours that are displayed on the MRI m-mode for visual assessment of accuracy. FIG. 4(A) illustrates the projection line, while FIG. 4(B) depicts an MRI m-mode image, with automatically detected contours. Wall thickness based on the calculated contours were also compared with thickness based on manually drawn contours as an initial validation step. FIG. 4(C1) illustrates automatic vs. manual wall thickness for the upper myocardium in the m-mode image, and FIG. 4(C2) illustrates automatic vs. manual wall thickness for the lower myocardium in the m-mode image.

According to an embodiment of the invention, the active contour model was tested on twelve MRI m-mode series (4 projections in each of 3 subjects). The visual qualitative inspection of the MRI m-mode-derived contours on the MRI m-mode display showed good correspondence. Average regional wall thickness was in the range from 7.1-11.8 mm as expected for normal wall thickness. The following table presents average and standard deviation values of the minimum and maximum wall thickness of the myocardium and septum over all cardiac cycles in one m-mode series for 3 volunteers.

| Volunteer | Min. wall thickness | Max. wall thickness |
|---|---|---|
| 1 (myocardium/lung) | 5.51 mm +/− 0.70 mm | 16.53 mm +/− 0.74 mm |
| 1 (Septum) | 5.13 mm +/− 0.49 mm | 9.86 mm +/− 1.26 mm |
| 2 (myocardium/lung) | 6.15 mm +/− 0.68 mm | 15.54 mm +/− 0.68 mm |
| 2 (Septum) | 5.3 mm +/− 0.9 mm | 8.6 mm +/− 0.9 mm |
| 3 (myocardium/lung) | 9.6 mm +/− 0.6 mm | 15.9 mm +/− 0.5 mm |
| 3 (Septum) | 3.5 mm +/− 1.7 mm | 10.2 mm +/− 1 mm |

In general, good correlation between the manual and automated contours was found, with the exception of some points in late diastole where rapid wall motion made manual identification of contours difficult.

According to another embodiment of the invention, interleaved real-time cardiac monitoring can be used to monitor perfusion. Beams, such as those described above in connection with ejection fraction, are projected through the heart in real time images and analyzed with respect to their signal-time behavior over a pre-determined time (typically 60 seconds) after intravenous administration of a contrast agent. The perfusion-related parameters derived from this signal-intensity time behavior, such as slope or area under the curve, or absolute blood flow in mL/min/100 g can be compared to previously determined parameter behavior. Alternatively, the individual pixels in the image can be analyzed with respect to their signal-intensity time behavior, and parametric maps of the semi-quantitative parameters can be made.

Figure 6:
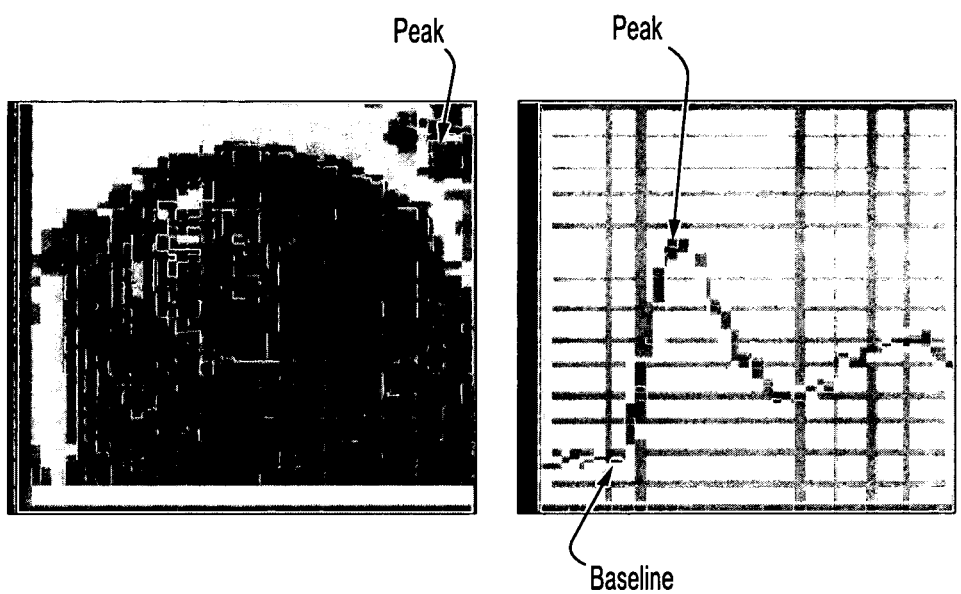
FIGS. 6(A)-(B) depict a parametric map of a short axis slice and a signal-intensity time curve from an individual pixel in the slice, according to an embodiment of the invention.

FIG. 6(A) depicts a parametric map of a short axis slice where the color of each pixel is related to the peak signal intensity achieved in that location during the first pass of a contrast agent. The peak signal intensity is proportional to the tissue perfusion so that areas of normal perfusion can be distinguished from those with abnormal perfusion, as indicated by the bright rim extending from 8-12 o'clock in the myocardium. FIG. 6(B) depicts the signal-intensity time curve from an individual pixel at the slice location shown in 6(A), with the baseline and peak points identified.

According to another embodiment of the invention, interleaved real-time cardiac monitoring can be used to monitor cardiac flow. In the case where a pencil beam 2D excitation is used, the phase of the MRI signal, encoded for velocity, is displayed as a function of time. Parameters related to the performance of the ventricle, such as time to peak flow, percentage regurgitant flow, peak flow velocity, etc., may be derived. In the case where a 2D image that is flow encoded replaces the 2D pencil beam excitation, segmentation methods may be applied to the portion of the image containing the part of the heart of interest, such as the aortic valve, and parameters can be derived from a subselection of the image.

Methods according to an embodiment of the invention for detecting changes in features in the derived data can be used to alert a physician that heart function is changing. For example, trend analysis can be used to determine if the ejection fraction is significantly changing over time, or with respect to a certain timepoint in the procedure specified by the operator, for example, baseline compared to time of stent placement.

According to another embodiment of the invention, change detection can be applied either to the absolute value of the extracted physiological parameter, or to the changes over time in either the raw data or the extracted parameters.

For each feature derived from the monitoring images, a clinically relevant threshhold can be determined. For example, for ejection fraction, a 5% change might be considered significant. A running average over the past n number of heartbeats would be maintained, and the parameter value at each heartbeat would be compared to the running average for detection of a change. In an alternative embodiment of the invention, each heartbeat can be compared to a baseline value at the beginning of the exam.

Change analysis or trend analysis in continuous signals is common in monitoring equipment. However, an embodiment of the invention can provide the raw data in terms of images prior to deriving features from the images and can develop change detection methods for the images or intermediate steps as well. For example, cross correlation analysis can be used to detect portions of the image that have changed since a pre-defined time.

It is to be understood that embodiments of the invention can be implemented in various forms of hardware, software, firmware, special purpose processes, or a combination thereof. In one embodiment, the invention can be implemented in software as an application program tangible embodied on a computer readable program storage device. The application program can be uploaded to, and executed by, a machine comprising any suitable architecture.

Figure 7:
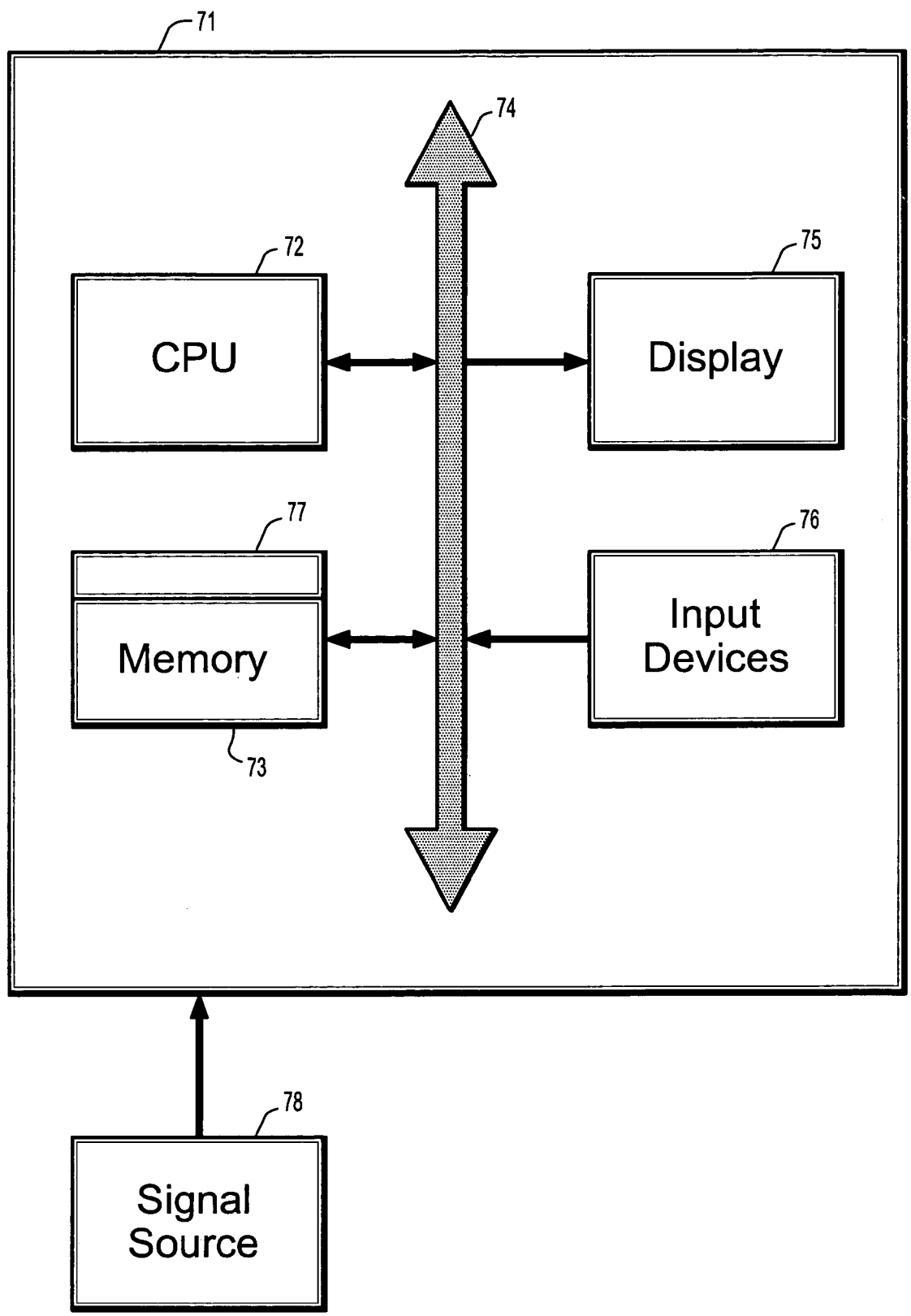
FIG. 7 is a block diagram of an exemplary computer system for implementing a method for real-time monitoring of heart function using magnetic resonance imaging (MRI), according to an embodiment of the invention.

FIG. 7 is a block diagram of an exemplary computer system for implementing a real time image-based cardiac monitoring method according to an embodiment of the invention. Referring now to FIG. 7, a computer system 71 for implementing the present invention can comprise, inter alfa, a central processing unit (CPU) 72, a memory 73 and an input/output (I/O) interface 74. The computer system 71 is generally coupled through the I/O interface 74 to a display 75 and various input devices 76 such as a mouse and a keyboard. The support circuits can include circuits such as cache, power supplies, clock circuits, and a communication bus. The memory 73 can include random access memory (RAM), read only memory (ROM), disk drive, tape drive, etc., or a combinations thereof. The present invention can be implemented as a routine 77 that is stored in memory 73 and executed by the CPU 72 to process the signal from the signal source 78. As such, the computer system 71 is a general purpose computer system that becomes a specific purpose computer system when executing the routine 77 of the present invention.

The computer system 71 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A computer implemented method for real time monitoring of cardiac function, the method performed by the computer comprising the steps of:
    selecting a plane through a heart from which to acquire heart function data;
    locating a center of a chamber of said heart;
    acquiring a sequence of 2D magnetic resonance (MR) images from said plane over one or more cardiac cycles with a time resolution at least one order of magnitude less than the cardiac rate, wherein each of said images comprises a plurality of intensities defined on a domain of points on a 2D grid;
    projecting a plurality of beams from said chamber center through each MR image as each MR image is acquired, each beam comprising a substantially collinear subset of points in said image;
    sampling image intensities along periodically spaced points of each beam in each MR image;
    obtaining image intensity in real-time as a function of time at corresponding beam points across the acquired MR images, wherein a time resolution of the image intensity function is at least that of the sequence of the 2D MR images;
    detecting endocardial contours from said image intensity functions sampled at periodically spaced points of each of the plurality of beams in each MR image;
    calculating distances between said detected endocardial contours, wherein the maximum distances as a function of time in each projection beam are taken as the end-diastolic (ED) diameter, and the minimum distances are taken as the end-systolic (ES) diameter; and
    using said image intensity time function along each said beam to detect changes in values of a physiological parameter over time.

2. The method of claim 1, further comprising bilinearly interpolating additional intensities between sampled points along each said beam.

3. The method of claim 1, wherein said endocardial contour is detected using a horizontal 1D Canny filter.

4. The method of claim 1, wherein said endocardial contour is detected using an active contour model that minimizes an energy that is a weighted sum of external constraint forces determined by said image and internal constraint forces that depend on the shape of the contour.

5. The method of claim 1, further comprising calculating a chamber area from the area enclosed by the points of the endocardial contour, and calculating an ejection fraction from EDV-ESV/EDV, wherein EDV is the end-diastolic chamber area and ESV is the end-systolic chamber area.

6. The method of claim 5, wherein said chamber is the left ventricle.

7. The method of claim 1, further comprising detecting epicardial contours from said plurality of beams, and calculating a wall thickness as a function of time from said endocardial contours and said epicardial contours.

8. The method of claim 1, wherein detecting value changes comprises selecting a clinically relevant change threshold, maintaining a running average of said parameter values over a predetermined number of previous heartbeats, and comparing a parameter value at each heartbeat to either the running average value or a baseline value for said parameter.

9. The method of claim 1, wherein said acquired 2D MR images are part of a sequence of images that include images acquired for diagnostic purposes.

10. A computer implemented method for real time monitoring of cardiac function during an image guided interventional procedure, the method performed by the computer comprising the steps of:
    defining a plurality of mutually orthogonal planes through a heart from which to acquire heart imaging data for acquiring a time series of 2-dimensional images from said selected planes, wherein each said image comprises a plurality of intensities defined on a domain of points on a 2D grid;
    selecting a subset of said time series of images to provide imaging data for monitoring heart function, wherein said selected subset of images are to be acquired from a same plane, wherein said remaining unselected images are acquired from a different plane and are adapted for diagnostic purposes;
    acquiring said time series of images over one or more heart cycles, wherein an image is acquired from each of the plurality of planes at each acquisition time, alternating between acquiring images for monitoring heart function and acquiring images for diagnostic purposes, wherein every $n^{th}$ image acquired during each heart cycle is acquired for monitoring, wherein n is greater than or equal to 2, wherein image intensities are extracted from corresponding points across the acquired monitoring images as each monitoring image is acquired to define said image intensities as a function of time; and
    using said image intensity time functions along each said beam to detect changes in values of a physiological parameter over time.

11. The method of claim 10, further comprising, for each monitoring image,
    selecting a center of a chamber of said heart,
    projecting a plurality of beams into said image through said chamber center, each beam comprising a substantially collinear subset of points in said image, and sampling image intensities along each point of said beam, to obtain a series of time measurements wherein an image intensity along each said beam is plotted as a function of time.

12. The method of claim 11, further comprising, analyzing said image-intensity time behavior over a pre-determined time period after intravenous administration of a contrast agent.

13. The method of claim 10, wherein said images are magnetic resonance (MR) phase images, and
further comprising plotting a MR phase encoded for velocity as a function of time, and deriving performance parameters from said phase-time plot, including one or more of time to peak flow, percentage regurgitant flow, and peak flow velocity.

14. The method of claim 13, where each said phase image is a 1D image created by using a pencil beam 2D radio-frequency excitation to derive measurements from a column of tissue.

15. The method of claim 13, where each said phase image is a 2D image created from a velocity encoded MR image.

16. A program storage device readable by a computer, tangibly embodying a non-transitory program of instructions executable by the computer to perform the method steps for real time monitoring of cardiac function, said method comprising the steps of:
selecting a plane through a heart from which to acquire heart function data;
locating a center of a chamber of said heart;
acquiring a sequence of 2D magnetic resonance (MR) images from said plane over one or more cardiac cycles with a time resolution at least one order of magnitude less than the cardiac rate, wherein each of said images comprises a plurality of intensities defined on a domain of points on a 2D grid;
projecting a plurality of beams from said chamber center through each MR image as each MR image is acquired, each beam comprising a substantially collinear subset of points in said image;
sampling image intensities along periodically spaced points of each beam in each MR image;
obtaining image intensity in real-time as a function of time at corresponding beam points across the acquired MR images, wherein a time resolution of the image intensity function is at least that of the sequence of the 2D MR images;
detecting endocardial contours from said image intensity functions sampled at periodically spaced points of each of the plurality of beams in each MR image;
calculating distances between said detected endocardial contours, wherein the maximum distances as a function of time in each projection beam are taken as the end-diastolic (ED) diameter, and the minimum distances are taken as the end-systolic (ES) diameter; and
using said image intensity time function along each said beam to detect changes in values of a physiological parameter over time.

17. The computer readable program storage device of claim 16, the method further comprising bilinearly interpolating additional intensities between sampled points along each said beam.

18. The computer readable program storage device of claim 16, wherein said endocardial contour is detected using a horizontal 1D Canny filter.

19. The computer readable program storage device of claim 16, wherein said endocardial contour is detected using an active contour model that minimizes an energy that is a weighted sum of external constraint forces determined by said image and internal constraint forces that depend on the shape of the contour.

20. The computer readable program storage device of claim 16, the method further comprising calculating a chamber area from the area enclosed by the points of the endocardial contour, and calculating an ejection fraction from EDV-ESV/EDV, wherein EDV is the end-diastolic chamber area and ESV is the end-systolic chamber area.

21. The computer readable program storage device of claim 20, wherein said chamber is the left ventricle.

22. The computer readable program storage device of claim 16, the method further comprising detecting epicardial contours from said plurality of beams, and calculating a wall thickness as a function of time from said endocardial contours and said epicardial contours.

23. The computer readable program storage device of claim 16, wherein detecting value changes comprises selecting a clinically relevant change threshold, maintaining a running average of said parameter values over a predetermined number of previous heartbeats, and comparing a parameter value at each heartbeat to either the running average value or a baseline value for said parameter.

24. The computer readable program storage device of claim 16, wherein said acquired 2D MR images are part of a sequence of images that include images acquired for diagnostic purposes.

25. The computer readable program storage device of claim 16, the method further comprising analyzing said image-intensity time behavior over a pre-determined time period after intravenous administration of a contrast agent.

26. The computer readable program storage device of claim 16, wherein said images are magnetic resonance (MR) phase images, and the method further comprising plotting a MR phase encoded for velocity as a function of time, and deriving performance parameters from said phase-time plot, including one or more of time to peak flow, percentage regurgitant flow, and peak flow velocity.

27. The computer readable program storage device of claim 26, where each said phase image is a 1D image created by using a pencil beam 2D radio-frequency excitation to derive measurements from a column of tissue.

28. The computer readable program storage device of claim 26, where each said phase image is a 2D image created from a velocity encoded MR image.

* * * * *